United States Patent
Jeong (10) Patent No.: US 8,902,418 B2
(45) Date of Patent: Dec. 2, 2014

(54) BOARD INSPECTION METHOD

(71) Applicant: Koh Young Technology Inc., Seoul (KR)

(72) Inventor: Joong-Ki Jeong, Seoul (KR)

(73) Assignee: Koh Young Technology Inc., Seoul (KR)

( * ) Notice: Subject to any disclaimer, the term of this patent is extended or adjusted under 35 U.S.C. 154(b) by 0 days.

(21) Appl. No.: 14/073,230

(22) Filed: Nov. 6, 2013

(65) Prior Publication Data

US 2014/0132953 A1    May 15, 2014

(30) Foreign Application Priority Data

Nov. 12, 2012  (KR) .................... 10-2012-0127241

(51) Int. Cl.
    *G01N 21/00* (2006.01)
    *G01J 3/46* (2006.01)
    *G01N 21/956* (2006.01)
    *G01N 21/88* (2006.01)

(52) U.S. Cl.
    CPC ...... *G01N 21/956* (2013.01); *G01N 2021/8845* (2013.01); *G01N 2021/95646* (2013.01)
    USPC ...................................... 356/237.5; 356/402

(58) Field of Classification Search
    USPC .............................................. 356/237.5, 402
    See application file for complete search history.

(56) References Cited

U.S. PATENT DOCUMENTS

| | | | |
|---|---|---|---|
| 6,947,151 B2 * | 9/2005 | Fujii et al. ................. | 356/612 |
| 7,062,080 B2 * | 6/2006 | Oshiumi et al. ............. | 382/141 |
| 2001/0012107 A1 * | 8/2001 | Toh .................. | 356/601 |
| 2003/0099393 A1 * | 5/2003 | Oshiumi et al. ............. | 382/150 |
| 2012/0086950 A1 * | 4/2012 | Sho et al. ................ | 356/601 |

FOREIGN PATENT DOCUMENTS

| | | |
|---|---|---|
| JP | 2008-309580 | 12/2008 |
| KR | 10-2011-0002985 | 1/2011 |

* cited by examiner

*Primary Examiner* — Roy M Punnoose
(74) *Attorney, Agent, or Firm* — Kile Park Reed & Houtteman PLLC (57) ABSTRACT

In order to inspect a board, first, an inspection area including a solder joint is provided with a first light having a first color, a second light having a second color and a third light having a third color at a first inclination angle, a second inclination angle smaller than the first inclination angle and a third inclination angle smaller than the second inclination angle with respect to the board, respectively. Then, a color image of the inspection area is acquired according to the first light, the second light and the third light provided to the inspection area. Thereafter, it is inspected whether the solder joint is good or bad by using a color distribution in the color image. Then, the inspection result is verified by using pre-measured height information of the solder joint. Thus, an inspection error may be prevented.

12 Claims, 5 Drawing Sheets

BOARD INSPECTION METHOD

CROSS REFERENCE TO RELATED APPLICATION

This application claims priority from and the benefit of Korean Patent Applications No. 10-2012-0127241 filed on Nov. 12, 2012, which are hereby incorporated by reference for all purposes as if fully set forth herein.

BACKGROUND OF THE INVENTION

1. Field of the Invention

Exemplary embodiments of the present invention relate to a board inspection method. More particularly, exemplary embodiments of the present invention relate to a board inspection method for inspecting a solder joint.

2. Discussion of the Background

Generally, at least one printed circuit board (PCB) is employed in an electronic device, and various circuit components such as a circuit pattern, a connection pad part, a driver chip electrically connected to the connection pad part, etc. are mounted on the PCB.

The circuit component such as the driver chip is mounted on the PCB by using solder. In order for the circuit component to operate normally on the PCB, the circuit component is required to be formed good on the PCB, and thus an inspection apparatus is used to inspect whether the circuit component is formed good or bad.

The inspection apparatus typically performs an inspection by capturing an image of a portion at which the circuit component is mounted, and recently, an inspection apparatus using three-dimensional shape information is widely employed.

In order to inspect whether the circuit component is formed good on the PCB, it may be inspected whether a solder joint electrically connecting a terminal of the circuit component and the PCB with each other is formed good.

The methods of inspecting the solder joint includes a method of expecting a slope of a surface of a solder joint by using colors of lights provided to a camera through three stepped lightings of red, green and blue (RGB) colors having an incident angle different from each other, and performing an inspection using the slope.

However, when using the method, an inspection error may occur by surrounding conditions such as interference of surrounding light, interference of an adjacent component, etc., and an inspection error may also occur when a solder joint does not have a typical shape. Thus, a board inspection method, capable of preventing an inspection error without effects due to surrounding conditions such as interference of surrounding light, interference of an adjacent component, etc., and also preventing an inspection error when a solder joint does not have a typical shape, is requested.

SUMMARY OF THE INVENTION

Exemplary embodiments of the present invention provide a board inspection method capable of preventing an inspection error without effects due to surrounding conditions such as interference of surrounding light, interference of an adjacent component, etc., and also preventing an inspection error when a solder joint does not have a typical shape.

Additional features of the invention will be set forth in the description which follows, and in part will be apparent from the description, or may be learned by practice of the invention.

An exemplary embodiment of the present invention discloses a board inspection method. In the board inspection method, first, an inspection area including a solder joint of a component mounted on a board is provided with a first light having a first color, a second light having a second color different from the first color and a third light having a third color different from the first and second colors at a first inclination angle with respect to the board, a second inclination angle smaller than the first inclination angle with respect to the board and a third inclination angle smaller than the second inclination angle with respect to the board, respectively. Then, a color image of the inspection area is acquired according to the first light, the second light and the third light provided to the inspection area. Thereafter, it is inspected whether the solder joint is good or bad by using a color distribution in the color image. Then, the inspection result is verified by using pre-measured height information of the solder joint.

In an exemplary embodiment, inspecting whether the solder joint is good or bad by using a color distribution in the color image, may include calculating the number of pixels corresponding to the third color among pixels forming the color image of the inspection area, calculating a ratio of the number of pixels corresponding to the third color to the total number of pixels forming the color image of the inspection area, and judging the solder joint as good in case that the ratio exceeds a predetermined reference ratio and the solder joint as bad in case that the ratio does not exceed the predetermined reference ratio.

In an exemplary embodiment, only in the case that the solder joint is judged as good in inspecting whether the solder joint is good or bad by using a color distribution in the color image, verifying the inspection result by using pre-measured height information of the solder joint may be performed.

In an exemplary embodiment, in the case that the solder joint is judged as good in inspecting whether the solder joint is good or bad by using a color distribution in the color image, in verifying the inspection result by using pre-measured height information of the solder joint, the solder joint may be judged as bad when a height of the solder joint is smaller than a predetermined reference height.

In an exemplary embodiment, only in the case that the solder joint is judged as bad in inspecting whether the solder joint is good or bad by using a color distribution in the color image, the inspection result may be verified by using pre-measured height information of the solder joint is performed.

In an exemplary embodiment, in the case that the solder joint is judged as bad in inspecting whether the solder joint is good or bad by using a color distribution in the color image, in verifying the inspection result by using pre-measured height information of the solder joint, the solder joint may be judged as good when a height of the solder joint is greater than a predetermined reference height.

For example, the first light, the second light and the third light may be a red light (R), a green light (G) and a blue light (B), respectively.

In an exemplary embodiment, the board inspection method may further include acquiring height information of the solder joint. Acquiring height information of the solder joint may include acquiring measurement data for the inspection area by providing a grating pattern light on the board by N times, wherein N is a natural number greater than or equal to 2, and acquiring the height information of the solder joint by applying a bucket algorithm to the measurement data.

Another exemplary embodiment of the present invention discloses a board inspection method. In the board inspection method, first, an inspection area including a solder joint of a component mounted on a board is provided with a plurality of lights having a color different from each other at an inclination angle different from each other with respect to the board. Then, a color image of the inspection area is acquired according to the plurality of lights provided to the inspection area. Thereafter, it is inspected whether the solder joint is good or bad by using a color distribution in the color image. Then, the inspection result is verified by using pre-measured height information of the solder joint.

In an exemplary embodiment, inspecting whether the solder joint is good or bad by using a color distribution in the color image, may include calculating the number of pixels corresponding to the color of the light having the smallest inclination angle of the lights, among pixels forming the color image of the inspection area, calculating a ratio of the number of pixels corresponding to the color of the light having the smallest inclination angle to the total number of pixels forming the color image of the inspection area, and judging the solder joint as good in case that the ratio exceeds a predetermined reference ratio and the solder joint as bad in case that the ratio does not exceed the predetermined reference ratio.

In an exemplary embodiment, in the case that the solder joint is judged as good in inspecting whether the solder joint is good or bad by using a color distribution in the color image, in verifying the inspection result by using pre-measured height information of the solder joint, the solder joint may be judged as bad when a height of the solder joint is smaller than a predetermined reference height.

In an exemplary embodiment, in the case that the solder joint is judged as bad in inspecting whether the solder joint is good or bad by using a color distribution in the color image, in verifying the inspection result by using pre-measured height information of the solder joint, the solder joint may be judged as good when a height of the solder joint is greater than a predetermined reference height.

According to the present invention, a two-dimensional inspection result, which is obtained by a color distribution of a color image captured in an image acquiring section such as a camera through a plurality of color lightings such as lightings having RGB-three steps, is verified by using three-dimensional height information.

Thus, effects due to surrounding conditions such as interference of surrounding light, interference of an adjacent component, etc. may be reduced, thereby preventing an inspection error. In addition, an inspection error may be also prevented when a solder joint does not have a typical shape.

Thus, defect of the solder joint may be more precisely judged, thereby more precisely judging defect of the printed circuit board.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 1:
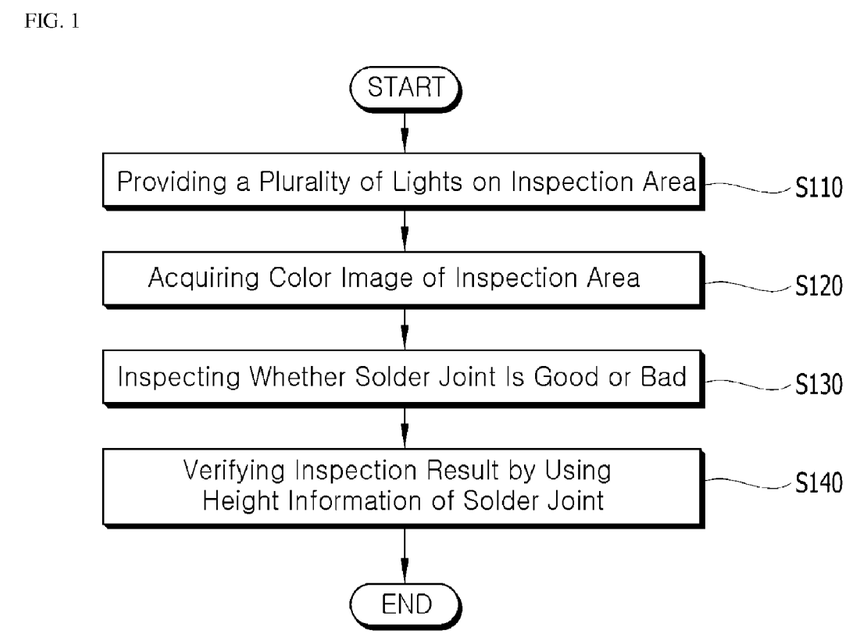
FIG. 1 is a flow chart illustrating a board inspection method according to an exemplary embodiment of the present invention.
Figure 2:
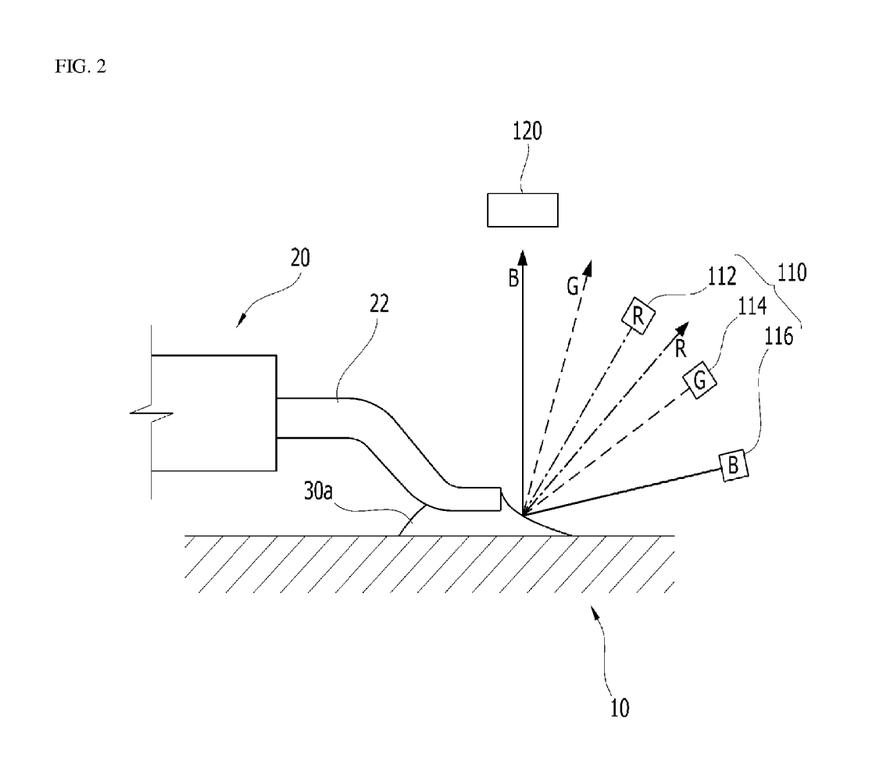
FIGS. 2 and 3 are conceptual views for explaining a board inspection method is according to an exemplary embodiment of the present invention.
Figure 3:
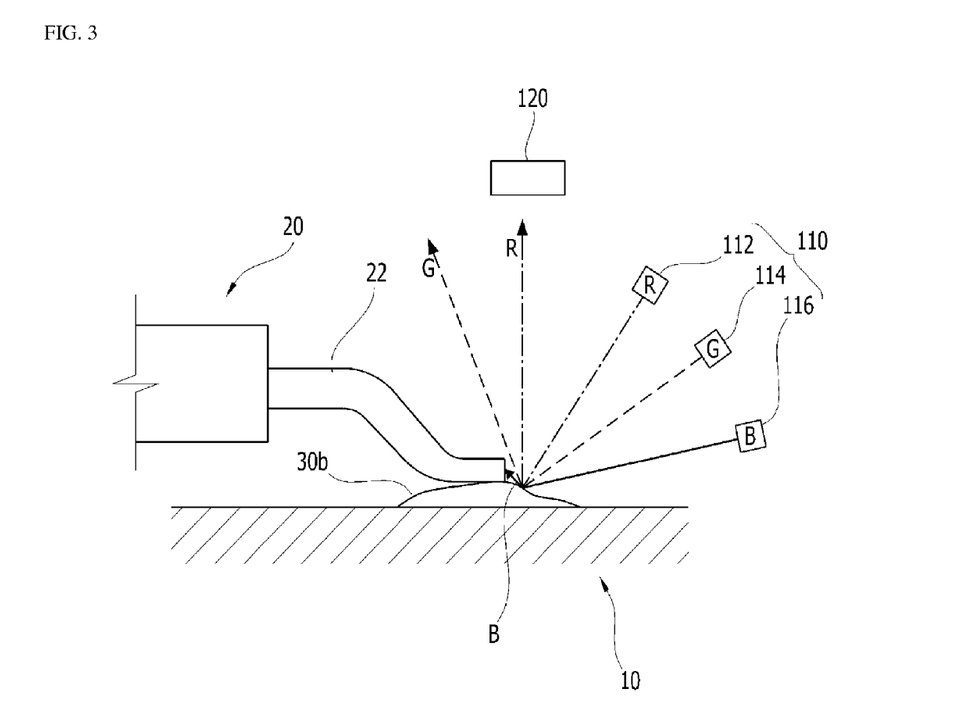

FIG. 1 is a flow chart illustrating a board inspection method according to an exemplary embodiment of the present invention. FIGS. 2 and 3 are conceptual views for explaining a board inspection method according to an exemplary embodiment of the present invention. FIG. 2 shows that a solder joint is good, and FIG. 3 shows that a solder joint is bad.

Referring to FIGS. 1 to 3, in order to inspect a board 10 according to an exemplary embodiment of the present invention, first, a plurality of lights is provided to an inspection area on the board 10 in step of S110.

Particularly, an inspection area including a solder joint 30a of a component 20 mounted on the board 10 is provided with a plurality of lights having a color different from each other at an inclination angle different from each other with respect to the board 10.

The inspection area corresponds to an area including an inspection target, and may be a region of interest (ROI) that may be manually established by a user or automatically established by an inspection apparatus. The solder joint 30a of the component 20 indicates a jointed portion of solder formed by jointing a terminal 22 of the component 20 and the solder when the component 20 is mounted on a printed circuit board using the solder.

In an exemplary embodiment, the lights are provided by a light-providing section 110, and may include a first light, a second light and a third light provided from a first light-providing section 112, a second light-providing section 114 and a third light-providing section 116, respectively. The first light, the second light and the third light may have a first color, a second light having a second color different from the first color and a third light having a third color different from the first and second colors. For example, the first color, the second color and the third color may be red, green and blue, respectively, and in FIGS. 2 and 3, the first light, the second light and the third light may be a red light R, a green light G and a blue light B.

In addition, as illustrated in FIGS. 2 and 3 in an exemplary embodiment, the first light R, the second light G and the third light B are provided to the board at a first inclination angle with respect to the board, a second inclination angle smaller than the first inclination angle with respect to the board and a third inclination angle smaller than the second inclination angle with respect to the board, respectively.

Then, a color image of the inspection area is acquired according to the plurality of lights provided to the inspection area in step of S120.

Particularly, the color image of the inspection area is acquired according to the first light R, the second light G and the third light B provided to the inspection area. In other words, as described above, the first light R, the second light G and the third light B having a color different from each other and an illumination angle different from each other are provided toward the solder joint 30a, and reflection lights enter an image acquiring section 120, for example, such as a camera, thereby acquiring the color image of the inspection area.

Thereafter, it is inspected whether the solder joint is good or bad by using a color distribution in the color image in step of S130.

That is, when using a distribution of colors shown in the acquired color image, a surface slope and/or a shape of the solder joint may be expected, to thereby inspect whether the solder joint is good or bad.

Typically, in case that the solder joint is formed good, as shown in FIG. 2, a slope of a surface of the solder joint 30a increases as near to the terminal 22, and the surface of the solder joint 30a is formed concave. In contrast, in case that the solder joint is formed bad, as shown in FIG. 3, a slope of a surface of the solder joint 30b decreases as near to the terminal 22, and the surface of the solder joint 30a is formed convex.

Thus, in case that the solder joint 30a is formed good, as shown in FIG. 2, a rate of the third light B is high in the color distribution in the color image, and in case that the solder joint 30b is formed bad, as shown in FIG. 3, a rate of the third light B is low in the color distribution in the color image.

Hence, in case that the rate of the third light B is high in the color distribution in the color image, it may be expected that the slope of the surface of the solder joint increases as near to the terminal 22 as shown in FIG. 2 and the surface of the solder joint is formed concave, thereby judging the solder joint 30a as good. In contrast, in case that the rate of the first light R is high in the color distribution in the color image, it may be expected that the slope of the surface of the solder joint decreases as near to the terminal 22 as shown in FIG. 3 and the surface of the solder joint is formed convex, thereby judging the solder joint 30a as bad.

In an exemplary embodiment, when inspecting whether the solder joint is good or bad by using the color distribution in the color image, the number of pixels of each color may be used.

Particularly, the number of pixels corresponding to the color of the light having the smallest inclination angle of the lights, among pixels forming the color image of the inspection area is calculated. Then, a ratio of the number of pixels corresponding to the color of the light having the smallest inclination angle to the total number of pixels forming the color image of the inspection area is calculated. Thereafter, it may be judged that the solder joint is good in case that the ratio exceeds a predetermined reference ratio, and the solder joint is bad in case that the ratio does not exceed the predetermined reference ratio.

For example, the number of pixels corresponding to the third color among pixels forming the color image of the inspection area is calculated. Then, a ratio of the number of pixels corresponding to the third color to the total number of pixels forming the color image of the inspection area is calculated. Thereafter, the solder joint may be judged as good in case that the ratio exceeds a predetermined reference ratio, and the solder joint may be judged as bad in case that the ratio does not exceed the predetermined reference ratio.

Then, the inspection result is verified by using pre-measured height information of the solder joint in step of S140.

As described above, when judging whether the solder joint is good or bad, the judgment may not be correct by surrounding conditions such as interference of light around the solder joint, interference of an adjacent component, etc. Thus, the inspection result may be verified.

Figure 4:
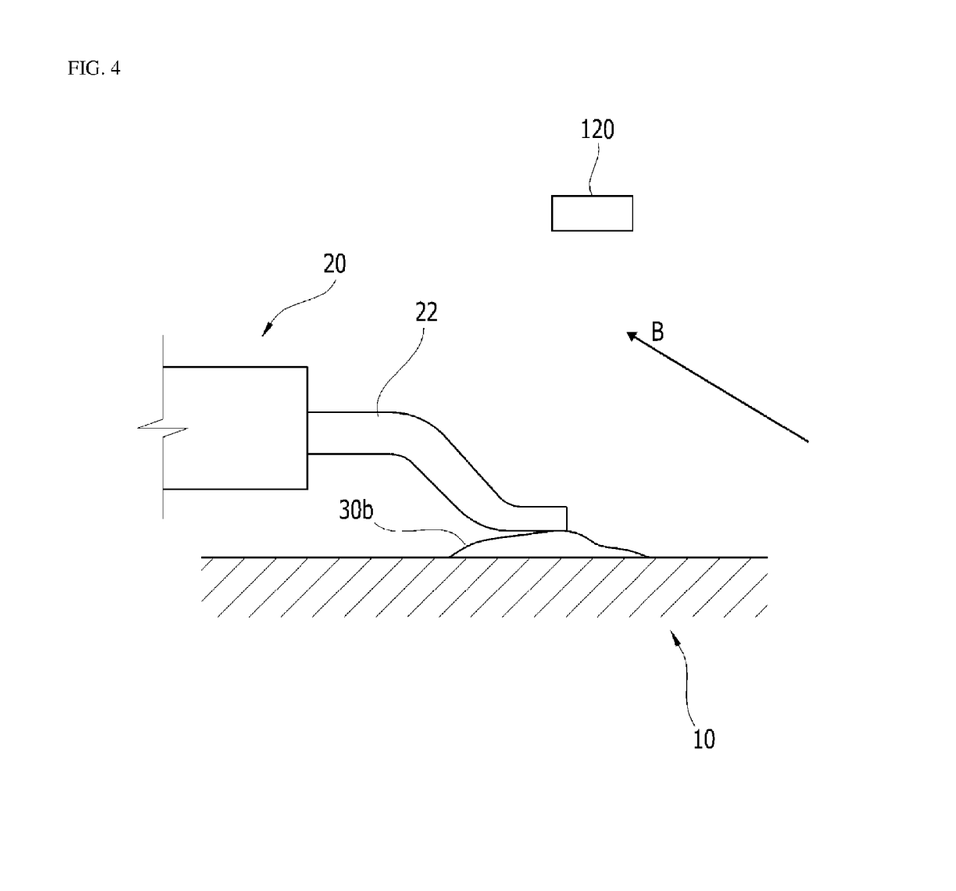
FIG. 4 is a conceptual view illustrating an example that a solder joint is judged as good in spite of bad when inspecting a solder joint in FIG. 1.

FIG. 4 is a conceptual view illustrating an example that a solder joint is judged as good in spite of bad when inspecting a solder joint in FIG. 1.

Referring to FIG. 4, although the solder joint is bad as shown in FIG. 3, since a blue light may be externally provided to the image acquiring section 120 by surrounding conditions such as interference of light around the solder joint, interference of an adjacent component, etc., the number of blue pixels in the color image acquired in the image acquiring section 120 may not be considered as the result due to the solder joint 30b (pollution of blue pixels). Thus, the inspection result may be judged as good in spite of bad.

In order to prevent the above error, the inspection result is verified by using pre-measured height information of the solder joint. In this case, information that is pre-acquired by using an inspection apparatus such as a three-dimensional measurement apparatus may be used as the height information of the solder joint.

In an exemplary embodiment, the height information of the solder joint may be acquired by using the three-dimensional measurement apparatus. That is, first, grating pattern lights are provided on the board 10 by N times to acquire measurement data of the inspection area (N is a natural number greater than or equal to 2), and then the height information of the solder joint may be acquired by applying a bucket algorithm to the acquired measurement data.

Since the three-dimensional measurement apparatus acquires information related to three-dimensional shape including height information so as to judge various defects of the board 10 having various components mounted thereon, the inspection result may be easily verified when using hereby acquired height information of the solder joint.

In an exemplary embodiment, even in case that the solder joint 30b is pre-judged as good, the solder joint 30b may be judged as bad when the height of the solder joint 30b is smaller than a predetermined reference height by using the pre-measured height information of the solder joint 30b.

Thus, as described above, through performing verifying the inspection result in step of S140, the inspection error may be prevented even in case that correct judgment is difficult due to surrounding conditions such as interference of light around the solder joint, interference of an adjacent component, etc.

Figure 5:
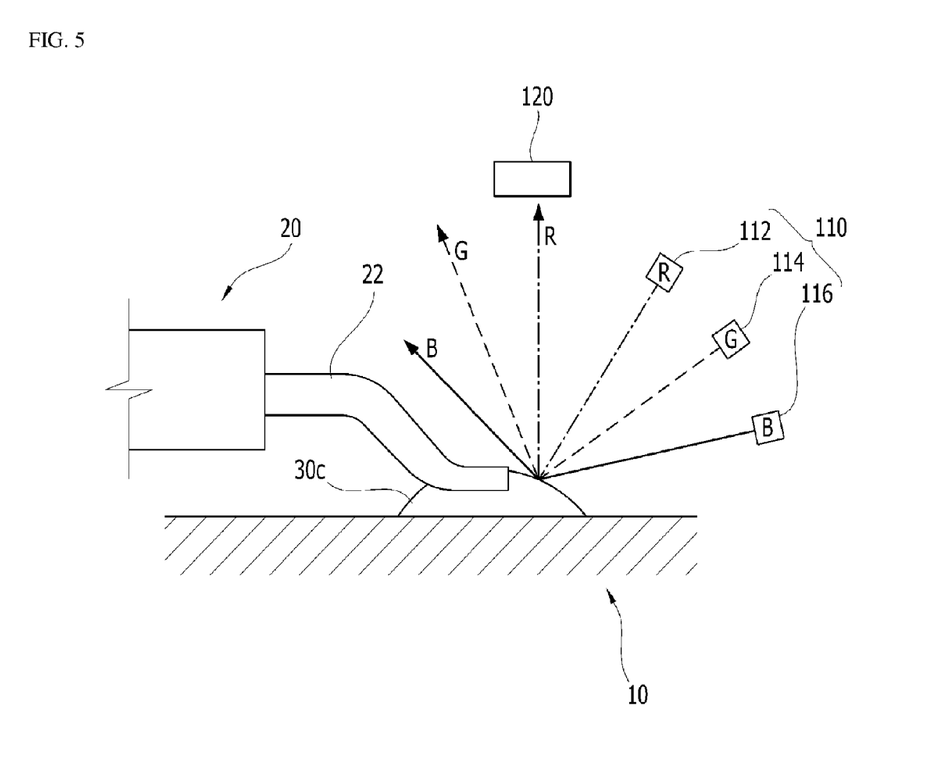
FIG. 5 is a conceptual view illustrating an example that a solder joint is judged as bad in spite of good when inspecting a solder joint in FIG. 1.

FIG. 5 is a conceptual view illustrating an example that a solder joint is judged as bad in spite of good when inspecting a solder joint in FIG. 1.

Referring to FIG. 5, although solder is formed enough to judge the solder joint 30c as good, since the shape of the solder joint 30c has a gentle slope which is different from general cases, the number of blue pixels in the color image acquired from the image acquiring section 120 is small in comparison with the case illustrated in FIG. 2. Thus, the inspection result may be judged as may be bad in spite of good.

In order to prevent the above error, the inspection result is verified by using pre-measured height information of the solder joint. In this case, information that is pre-acquired by using an inspection apparatus such as a three-dimensional measurement apparatus may be used as the height information of the solder joint.

In an exemplary embodiment, the height information of the solder joint may be acquired by using the three-dimensional measurement apparatus. That is, first, grating pattern lights are provided on the board 10 by N times to acquire measurement data of the inspection area (N is a natural number greater than or equal to 2), and then the height information of the solder joint may be acquired by applying a bucket algorithm to the acquired measurement data.

Since the three-dimensional measurement apparatus acquires information related to three-dimensional shape including height information so as to judge various defects of the board 10 having various components mounted thereon, the inspection result may be easily verified when using hereby acquired height information of the solder joint.

In an exemplary embodiment, even in case that the solder joint 30c is pre-judged as bad, the solder joint 30c may be judged as good when the height of the solder joint 30c is greater than a predetermined reference height by using the pre-measured height information of the solder joint 30c.

Thus, as described above, through performing verifying the inspection result in step of S140, the inspection error may be prevented even in case that the solder joint does not have a general shape.

Verifying the inspection result in step of S140 may be selectively performed in one case of pre-judging the solder joint as good and pre-judging the solder joint as bad.

Generally, when many printed circuit boards having the same type correspond to an inspection target, solder joints formed at the identical components of the same typed printed circuit boards have substantially the same surrounding conditions. Thus, when the inspection error described in FIG. 4 occurs frequently at sampled printed circuit boards, verifying the inspection result in step of S140 may be performed only in case that the inspection result of the solder joint is judged as good.

In addition, when many printed circuit boards having the same type correspond to an inspection target, the same solder paste forming apparatus and the same reflow apparatus are used, and thus the inspection error described in FIG. 5 may occur frequently, while the inspection error described in FIG. 4 does not occur frequently. Thus, when the inspection error described in FIG. 5 occurs frequently at sampled printed circuit boards, verifying the inspection result in step of S140 may be performed only in case that the inspection result of the solder joint is judged as bad.

As a result, when many printed circuit boards having the same type correspond to an inspection target, the frequency number of the inspection error described in FIG. 4 and the frequency number of the inspection error described in FIG. 5 are checked at sampled printed circuit boards, and verifying the inspection result in step of S140 may be selectively performed in case that only one case occurs or any one case occurs still more frequently.

According to the present invention as described above, a two-dimensional inspection result, which is obtained by a color distribution of a color image captured in an image acquiring section such as a camera through a plurality of color lights such as lightings having RGB-three steps, is verified by using three-dimensional height information.

Thus, effects due to surrounding conditions such as interference of surrounding light, interference of an adjacent component, etc. may be reduced, thereby preventing an inspection error. In addition, an inspection error may be also prevented when a solder joint does not have a typical shape.

Thus, defect of the solder joint may be more precisely judged, thereby more precisely judging defect of the printed circuit board.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A board inspection method comprising:
   providing an inspection area including a solder joint of a component mounted on a board with a first light having a first color, a second light having a second color different from the first color and a third light having a third color different from the first and second colors at a first inclination angle with respect to the board, a second inclination angle smaller than the first inclination angle with respect to the board and a third inclination angle smaller than the second inclination angle with respect to the board, respectively;
   acquiring a color image of the inspection area according to the first light, the second light and the third light provided to the inspection area;
   inspecting whether the solder joint is good or bad by using a color distribution in the color image; and
   verifying the inspection result by using pre-measured height information of the solder joint.

2. The board inspection method of claim 1, wherein inspecting whether the solder joint is good or bad by using a color distribution in the color image, comprising:
   calculating the number of pixels corresponding to the third color among pixels forming the color image of the inspection area;
   calculating a ratio of the number of pixels corresponding to the third color to the total number of pixels forming the color image of the inspection area; and
   judging the solder joint as good in case that the ratio exceeds a predetermined reference ratio, and the solder joint as bad in case that the ratio does not exceed the predetermined reference ratio.

3. The board inspection method of claim 1, wherein only in the case that the solder joint is judged as good in inspecting whether the solder joint is good or bad by using a color distribution in the color image,
   verifying the inspection result by using pre-measured height information of the solder joint is performed.

4. The board inspection method of claim 1, wherein in the case that the solder joint is judged as good in inspecting whether the solder joint is good or bad by using a color distribution in the color image,
   in verifying the inspection result by using pre-measured height information of the solder joint, the solder joint is judged as bad when a height of the solder joint is smaller than a predetermined reference height.

5. The board inspection method of claim 1, wherein only in the case that the solder joint is judged as bad in inspecting whether the solder joint is good or bad by using a color distribution in the color image,
   verifying the inspection result by using pre-measured height information of the solder joint is performed.

6. The board inspection method of claim 1, wherein in the case that the solder joint is judged as bad in inspecting whether the solder joint is good or bad by using a color distribution in the color image,
   in verifying the inspection result by using pre-measured height information of the solder joint, the solder joint is judged as good when a height of the solder joint is greater than a predetermined reference height.

7. The board inspection method of claim 1, wherein the first light, the second light and the third light are a red light (R), a green light (G) and a blue light (B), respectively.

8. The board inspection method of claim 1, further comprising acquiring height information of the solder joint,
   wherein acquiring height information of the solder joint comprising:
   acquiring measurement data for the inspection area by providing a grating pattern light on the board by N times, wherein N is a natural number greater than or equal to 2; and
   acquiring the height information of the solder joint by applying a bucket algorithm to the measurement data.

9. A board inspection method comprising:
   providing an inspection area including a solder joint of a component mounted on a board with a plurality of lights having a color different from each other at an inclination angle different from each other with respect to the board,
   acquiring a color image of the inspection area according to the plurality of lights provided to the inspection area;
   inspecting whether the solder joint is good or bad by using a color distribution in the color image; and
   verifying the inspection result by using pre-measured height information of the solder joint.

10. The board inspection method of claim 9, wherein inspecting whether the solder joint is good or bad by using a color distribution in the color image, comprising:
    calculating the number of pixels corresponding to the color of the light having the smallest inclination angle of the lights, among pixels forming the color image of the inspection is area;
    calculating a ratio of the number of pixels corresponding to the color of the light having the smallest inclination angle to the total number of pixels forming the color image of the inspection area; and
    judging the solder joint as good in case that the ratio exceeds a predetermined reference ratio, and the solder joint as bad in case that the ratio does not exceed the predetermined reference ratio.

11. The board inspection method of claim 9, wherein in the case that the solder joint is judged as good in inspecting whether the solder joint is good or bad by using a color distribution in the color image,
    in verifying the inspection result by using pre-measured height information of the solder joint, the solder joint is judged as bad when a height of the solder joint is smaller than a predetermined reference height.

12. The board inspection method of claim 9, wherein in the case that the solder joint is judged as bad in inspecting whether the solder joint is good or bad by using a color distribution in the color image,
    in verifying the inspection result by using pre-measured height information of the solder joint, the solder joint is judged as good when a height of the solder joint is greater than a predetermined reference height.

* * * * *